United States Patent
Koos et al.

(10) Patent No.: US 11,053,503 B2
(45) Date of Patent: Jul. 6, 2021

(54) METHODS AND MEANS OF GENERATING IL-17 ASSOCIATED ANTITUMOR EFFECTOR CELLS BY INHIBITION OF NR2F6 INHIBITION

(71) Applicant: Regen Biopharma, Inc, La Mesa, CA (US)

(72) Inventors: David Koos, La Mesa, CA (US); Thomas Ichim, San Diego, CA (US); Santosh Kesari, Pacific Palisades, CA (US)

( * ) Notice: Subject to any disclaimer, the term of this patent is extended or adjusted under 35 U.S.C. 154(b) by 171 days.

(21) Appl. No.: 15/431,681

(22) Filed: Feb. 13, 2017

(65) Prior Publication Data
US 2017/0362596 A1 Dec. 21, 2017

Related U.S. Application Data

(60) Provisional application No. 62/294,007, filed on Feb. 11, 2016.

(51) Int. Cl.
| | |
|---|---|
| *C12N 15/113* | (2010.01) |
| *C12N 5/0783* | (2010.01) |
| *A61K 35/17* | (2015.01) |
| *C12N 5/0786* | (2010.01) |

(52) U.S. Cl.
CPC .......... *C12N 15/1138* (2013.01); *A61K 35/17* (2013.01); *C12N 5/0638* (2013.01); *C12N 15/113* (2013.01); *C12N 2310/14* (2013.01); *C12N 2310/315* (2013.01); *C12N 2310/32* (2013.01); *C12N 2310/3341* (2013.01); *C12N 2501/60* (2013.01); *C12N 2502/1157* (2013.01)

(58) Field of Classification Search
None
See application file for complete search history.

(56) References Cited

U.S. PATENT DOCUMENTS

| | | | | |
|---|---|---|---|---|
| 2010/0135990 A1* | 6/2010 | Ichim | ................... | A61K 31/00 424/130.1 |
| 2011/0236427 A1* | 9/2011 | Baier | ................. | C12N 15/1138 424/277.1 |
| 2015/0203846 A1* | 7/2015 | Ichim | .................. | C12N 15/113 424/450 |

OTHER PUBLICATIONS

Elton et al (EXCLI Journal 2015;14:758-790) (Year: 2015).*
Hermann-Kleiter et al (Cell Reports 12, 2072-2085, Sep. 29, 2015) (Year: 2015).*
Warnecke et al (Genes & Development 19:614-625, 2005) (Year: 2005).*
Shu et al (Eur. J. Innnnunol. 1995.25: 1125-1128) (Year: 1995).*
Wittmann et al (J Allergy Clin Immunol 2004;114:965-73) (Year: 2004).*
Qian et al (Cytokine 89 (2017) 34-44) (Year: 2017).*
Zhao (Eur. J. Immunol. 2011, 41: 2314-2322) (Year: 2011).*
Zhang et al (Gastroenterology 2012;143:951-962) (Year: 2012).*
Perica et al (Rambam Mainnonides Med J 6(1):e0004, 2015, 9 pages) (Year: 2015).*
Wang et al (Immunotherapy (2014) 6(12), 1265-1278) (Year: 2014).*
Yong et al (Immunology and Cell Biology (Dec. 2016) 95: 356-363) (Year: 2016).*

* cited by examiner

*Primary Examiner* — Richard A Schnizer
(74) *Attorney, Agent, or Firm* — Baumgartner Patent Law; Marc Baumgartner

(57) ABSTRACT

Disclosed are means, methods, and compositions of matter useful for generation of cancer inhibitory effector cells producing interleukin-17 (IL-17). In one embodiment a cellular population is obtained, said cellular population is exposed to agents capable of inhibiting NR2F6, whereby said inhibition of NR2F6 results in upregulation of IL-17 production, said upregulation of IL-17 production associated with acquisition of anti-tumor activity.

8 Claims, 1 Drawing Sheet
Specification includes a Sequence Listing.

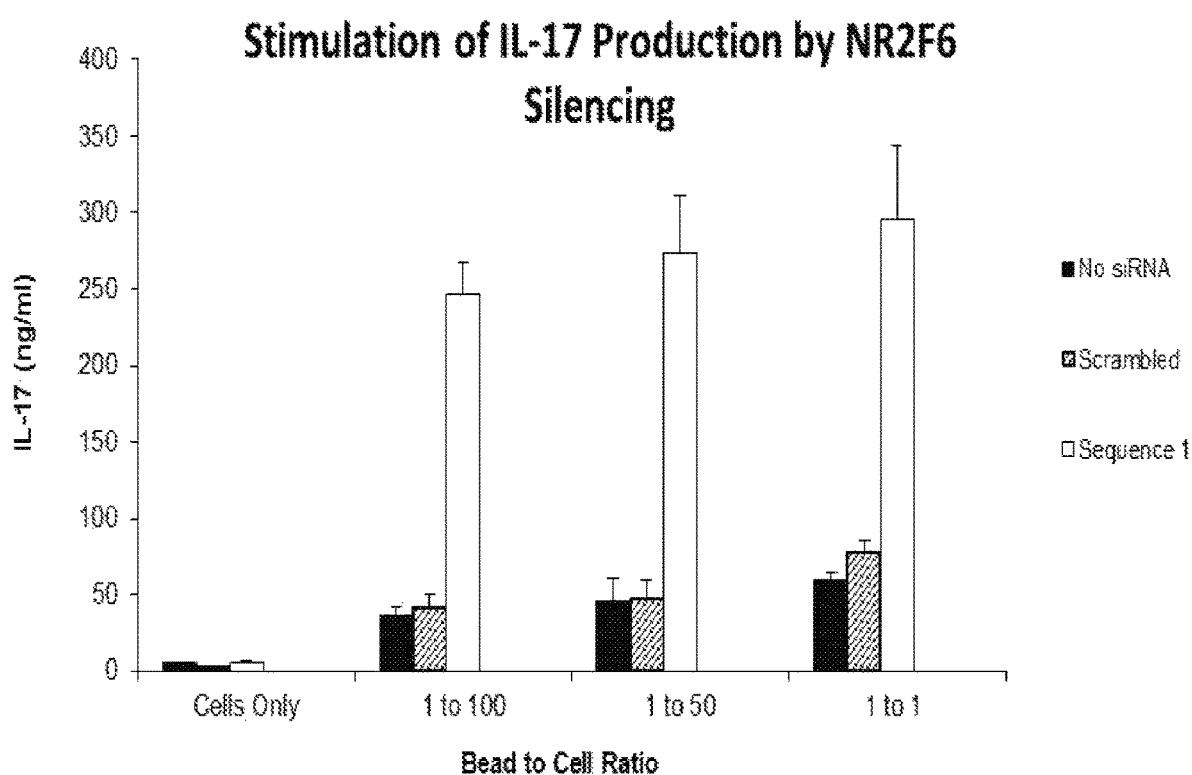

METHODS AND MEANS OF GENERATING IL-17 ASSOCIATED ANTITUMOR EFFECTOR CELLS BY INHIBITION OF NR2F6 INHIBITION

CROSS-REFERENCE TO RELATED APPLICATIONS

This application claims benefit of priority to U.S. Provisional Application No. 62/294,007 filed Feb. 11, 2016, the contents of which are hereby incorporated by reference.

SEQUENCE LISTING

The instant application contains a Sequence Listing which has been submitted electronically in ASCII format and is hereby incorporated by reference in its entirety. Said ASCII copy, created on Aug. 30, 2017, is named RegenIL-17-NP1_SL.txt and is 975 bytes in size.

SEQUENCE LISTING

```
SEQ ID NO 1:
GAT CCG CAT TAC GGT GTC TTC ACC TTC AAG AGA GGT

GAA GAC ACC GTA ATG CTT TTT TCT AGA G

SEQ ID NO 2:
GAT CCG CCT CTG GAC ACG TAA CCT ATT CAA GAG ATA

GGT TAC GTG TCC AGA GGT TTT TTC TAG AG
```

FIELD OF THE INVENTION

The invention pertains to stimulation of immunity to cancer antigens, particularly the invention pertains to utilization of NR2F6 inhibition to augment T cell activation, more particularly the invention relates to stimulation of IL-17 dependent immune responses to inhibit and reverse growth of tumors.

BACKGROUND OF THE INVENTION

The immune system is comprised of multiple different cell types, biologically active compounds and molecules and organs. These include lymphocytes, monocytes and polymorphonuclear leukocytes, numerous soluble chemical mediators (cytokines and growth factors), the thymus, postnatal bone marrow, lymph nodes, liver and spleen. All of these components work together through a complex communication system to fight against microbial invaders such as bacteria, viruses, fungi and parasites, and tumor cells. Together, these components recognize specific molecular antigens as foreign or otherwise threatening, and initiate an immune response against cells or viruses that contain the foreign antigen. The immune system also functions to eliminate damaged or cancerous cells through active surveillance using the same mechanisms used to recognize microbial or viral invaders. The immune system recognizes the damaged or cancerous cells via antigens that are not strictly foreign, but are aberrantly expressed or mutated in the targeted cells.

Unfortunately, while immunity to cancer cells has been demonstrated, this is not effective at a level sufficient to induce clinical responses in many cases. One method of augmenting immune response is to depress the self-regulatory mechanisms that the immune responses uses to regulate itself. Inhibition of inhibitory signals, called "checkpoint inhibitors" have demonstrated promising clinical efficacy in numerous situations. Despite this, a considerable number of patients do not respond to checkpoint inhibitors, or possess grave toxicities. In the current invention we disclose a novel immunological checkpoint, NR2F6, and mechanisms of antitumor activity.

BRIEF DESCRIPTION OF THE DRAWINGS

FIG. 1 is a bar graph showing augmentation of T cell IL-17 induced by anti-CD3 and anti-CD28 was achieved by inhibition of NR2F6.

DETAILED DESCRIPTION

Aspect 1. A cellular population capable of inhibiting cancer, said cellular population modulated to express lower levels of NR2F6 as compared to non-manipulated cellular population, wherein said lower level of NR2F6 is associated with augmentation of IL-17, wherein said IL-17 production is associated with reduction of tumor activity.

Aspect 2. The cellular population of Aspect 1, wherein said cellular population capable of inhibiting cancer is an immune cell.

Aspect 3. The cellular population of Aspect 2, wherein said immune cell is a T cell.

Aspect 4. The cellular population of Aspect 3, wherein said T cell is activated with a mitogenic signal.

Aspect 5. The cellular population of Aspect 3 wherein said T cell possesses phosphorylated immunoreceptor signalling motifs (ITAMs)

Aspect 6. The cellular population of Aspect 1, wherein said IL-17 production is associated with activation of macrophages.

Aspect 7. The cellular population of Aspect 6, wherein said activation of macrophages occurs in tumor associated macrophages.

Aspect 8. The cellular population of Aspect 7, wherein said tumor associated macrophages express the enzyme arginase.

Aspect 9. The cellular population of Aspect 7, wherein said tumor associated macrophages express the enzyme indolamine 2,3 deoxygenase.

Aspect 10. The cellular population of Aspect 8, wherein said arginase expression is reduced by said IL-17 produced by said cellular population capable of inhibiting cancer.

Aspect 11. The cellular population of Aspect 9, wherein said arginase expression is reduced by said IL-17 produced by said cellular population capable of inhibiting cancer.

Aspect 12. The cellular population of Aspect 1, wherein said IL-17 production is associated with activation of neutrophils.

Aspect 13. The cellular population of Aspect 12, wherein said activation of neutrophils is associated with IL-8 production.

Aspect 14. The cellular population of Aspect 12, wherein said activation of neutrophils is associated with reduction of apoptosis of said neutrophils.

Aspect 15. The cellular population of Aspect 12, wherein said activation of neutrophils is associated with enhanced ability to perform antibody associated cellular cytotoxicity.

Aspect 16. The cellular population of Aspect 12, wherein said activation of neutrophils is associated with increased tumor cytotoxicity.

Aspect 17. The cellular population of Aspect 12, wherein said activation of neutrophils is associated with decreased ability to secrete VEGF.

Aspect 18. The cellular population of Aspect 12, wherein said activation of neutrophils is associated with decreased ability to secrete EGF.

Aspect 19. The cellular population of Aspect 12, wherein said activation of neutrophils is associated with decreased ability to secrete PDGF.

Aspect 20. The cellular population of Aspect 1, wherein said cellular population possesses ability to selectively migrate to hypoxic areas of the body.

Aspect 21. The cellular population of Aspect 20, wherein said cellular population is capable of migrating to SDF-1

Aspect 22. The cellular population of Aspect 20, wherein said cellular population is capable of migrating to CXCL-10.

Aspect 23. The cellular population of Aspect 21, wherein said population expresses the receptor CXCR4.

Aspect 24. The cellular population of Aspect 22, wherein said population expresses the receptor CXCR3.

Aspect 25. The cellular population of Aspect 20, wherein said population is capable of migrating to VEGF.

Aspect 26. The cellular population of Aspect 20, wherein said population is capable of migrating towards angiopoietin.

Aspect 27. The cellular population of Aspect 1, wherein said cellular population is peripheral blood mononuclear cells.

Aspect 28. The cellular population of Aspect 1, wherein said cellular population is a lymphocyte.

Aspect 29. The cellular population of Aspect 1, wherein said cellular population is a T cell.

Aspect 30. The cellular population of Aspect 1, wherein said T cell is a CD4 cell.

Aspect 31. The cellular population of Aspect 30, wherein said T cell is a Th1 cell Aspect 32. The cellular population of Aspect 31, wherein said Th1 cell is capable of secreting higher amounts of interferon gamma and less amounts of IL-4, as compared to naïve T cells.

Aspect 33. The cellular population of Aspect 31, wherein said Th1 cells express higher amounts of STAT4 as compared to naïve T cells.

Aspect 34. The cellular population of Aspect 31, wherein said Th1 cells express lower amounts of STAT6 as compared to naïve T cells.

Aspect 35. The cellular population of Aspect 31, wherein said Th1 cells express higher amounts of T-bet as compared to naïve T cells.

Aspect 37. The cellular population of Aspect 29, wherein said T cell is a naïve T cell.

Aspect 38. The cellular population of Aspect 29, wherein said T cell is a gamma delta T cell.

Aspect 39. The cellular population of Aspect 29, wherein said T cell is an NKT cell.

Aspect 40. The cellular population of Aspect 29, wherein said T cell is a T regulatory cell.

Aspect 41. The cellular population of Aspect 40, wherein said T regulatory cell is capable of suppressing proliferation of a naïve T cell activated with CD3 and CD28 binding antibodies.

Aspect 42. The cellular population of Aspect 40, wherein said T regulatory cell is capable of suppressing maturation of dendritic cells.

43. The cellular population of claim 42, wherein said maturation is dendritic cells is upregulation of molecules selected from a group comprising of: CD80; CD40; CD86; and HLA II.

Aspect 44. The cellular population of Aspect 40, wherein said T regulatory cell possesses expression of GITR ligand.

Aspect 45. The cellular population of Aspect 40, wherein said T regulatory cell expresses neuropilin-1.

Aspect 46. The cellular population of Aspect 40, wherein said T regulatory cell expresses CTLA-4.

Aspect 47. The cellular population of Aspect 40, wherein said T regulatory cell expresses CD25.

Aspect 48. The cellular population of Aspect 40, wherein said T regulatory cell expresses CD105.

Aspect 49. The cellular population of Aspect 40, wherein said T regulatory cell expresses membrane bound TGF-beta.

Aspect 50. The cellular population of Aspect 40, wherein said T regulatory cell produces IL-10.

Aspect 51. The cellular composition of Aspect 1, wherein said inhibition of NR2F6 is achieved by means selected from a group comprising of: a) antisense oligonucleotides; b) induction of RNA interference; c) small molecule inhibitors; d) aptamers; e) gene-editing; f) ribozymes; and g) decoy oligonucleotides.

Aspect 52. The cellular population of Aspect 51, wherein said antisense oligonucleotides are capable of blocking expression of NR2F6 through activation of RNAse H.

Aspect 53. The cellular population of Aspect 52, wherein said antisense oligonucleotides are 12 to 30 nucleotide bases in length and having a nucleotide sequence that is at least 90% complementary to an equal length portion of the human NR2F6 gene but not to other sequences throughout the human genome.

Aspect 54. The cellular population of Aspect 52, wherein at least one internucleoside linkage is a modified internucleoside linkage.

Aspect 55. The cellular population of Aspect 54, wherein each internucleoside linkage is a phosphorothioate internucleoside linkage.

Aspect 56. The cellular population of Aspect 53, wherein at least one nucleoside comprises a modified sugar.

Aspect 57. The cellular population of Aspect 56, wherein at least one modified sugar is a bicyclic sugar.

Aspect 58. The cellular population of Aspect 57, wherein the at least one bicyclic sugar comprises a 4'-CH(CH.sub.3)-O-2' bridge.

Aspect 59. The cellular population of Aspect 53, wherein at least one modified sugar comprises a 2'-O-methoxyethyl.

Aspect 60. The cellular population of Aspect 53, wherein at least one said nucleobase is a modified nucleobase.

Aspect 61. The cellular population of Aspect 60, wherein the modified nucleobase is a 5-methylcytosine.

Aspect 62. The cellular population of Aspect 51, wherein said RNA interference is induced by administration of a compound selected from a group comprising of: a) single-stranded small interfering molecules (ss-siRNA); b) short interfering RNA (siRNA); c) miRNA; and d) short hairpin RNA (shRNA).

Aspect 63. The cellular population of Aspect 62, wherein the sequence of said ss-siRNA molecule is sufficiently complementary to the human NR2F6 mRNA sequence to direct target-specific RNAi and wherein the 5' nucleotide is 5' phosphorylated or is capable of being 5' phosphorylated in situ or in vivo.

Aspect 64. The cellular population of Aspect 63, wherein said ss-siRNA is sufficiently complementary to a target NR2F6 mRNA, said target NR2F6 mRNA specifying the amino acid sequence of said NR2F6 protein.

Aspect 65. The cellular population of Aspect 64, wherein said ssRNA is modified such that said ss-siRNA has increased in situ or in vivo stability as compared to a corresponding unmodified ss-siRNA.

Aspect 66. The cellular population of Aspect 65, wherein said modified ss-siRNA is modified by the substitution of at least one nucleotide with a modified nucleotide.

Aspect 67. The cellular population of Aspect 66, wherein in said ss-siRNA the modified nucleotide is a sugar-modified nucleotide.

Aspect 68. The cellular population of Aspect 62, wherein said siRNA comprising a sense strand and an antisense strand, wherein the antisense strand has a sequence sufficiently complementary to a NR2F6 target mRNA sequence to direct target-specific RNAi.

Aspect 69. The cellular population of Aspect 62, wherein said siRNA comprising a sense strand and an antisense strand, wherein the antisense strand has a sequence sufficiently complementary to a NR2F6 target mRNA sequence to direct target-specific RNAi and wherein the sense strand or antisense strand is modified by the substitution of at least one internal nucleotide with a modified nucleotide, such that in vivo stability is enhanced as compared to a corresponding unmodified siRNA or such that the target efficiency is enhanced compared to a corresponding unmodified siRNA.

Aspect 70. The cellular population of Aspect 69, wherein the modified nucleotide is selected from the group consisting of (a) a sugar-modified nucleotide, (b) a nucleobase-modified nucleotide, (c) a 2'-deoxy ribonucleotide and is present within the sense strand (d) a 2'-fluoro modified ribonucleotide, (e) a modified nucleotide is selected from the group consisting of a 2'-fluoro, 2'-amino and 2'-thio modified ribonucleotide, (f) modified nucleotides which are a 2'-fluoro modified ribonucleotide (e.g., 2'-fluoro uridine or 2'-fluoro cytidine) and a 2'-deoxy ribonucleotide (e.g., 2'-deoxy adenosine or 2'-deoxy guanosine), (g) a modified nucleotide is selected from the group consisting of 2'-fluoro-cytidine, 2'-fluoro-uridine, 2'-fluoro-adenosine, 2'-fluoro-guanosine, 2'-amino-cytidine, 2'-amino-uridine, 2'-amino-adenosine, 2'-amino-guanosine and 2'-amino-butyryl-pyrene-uridine, (h) modified nucleotide is selected from the group consisting of 5-bromo-uridine, 5-iodo-uridine, 5-methyl-cytidine, ribo-thymidine, 2-aminopurine, 5-fluoro-cytidine, and 5-fluoro-uridine, 2,6-diaminopurine, 4-thio-uridine; and 5-amino-allyl-uridine, or (i) a backbone-modified nucleotide. (e.g., contains a phosphorothioate group).

Aspect 71. The cellular population of Aspect 69, wherein the modified nucleotide is a backbone-modified nucleotide that contains a phosphorothioate group.

Aspect 72. The cellular population of Aspect 69, wherein the sense strand is crosslinked to the antisense strand or wherein a 3' OH terminus of the sense strand or antisense strand is modified.

Aspect 73. The cellular population of Aspect 69, wherein said siRNA is between about 10 and 50 residues in length, between about 15 and 45 residues in length, between about 20 and 40 residues in length, or between about 18 and 25 residues in length.

Aspect 74. The cellular population of Aspect 69, wherein one strand of said siRNA is comprised of the nucleotide sequence: 5'-GAT CCG CAT TAC GGT GTC TTC ACC TTC AAG AGA GGT GAA GAC ACC GTA ATG CTT TTT TCT AGA G-3' (SEQ ID NO: 1)

Aspect 75. The cellular population of Aspect 69, wherein one strand of said siRNA is comprised of the nucleotide sequence: 5'-GAT CCG CCT CTG GAC ACG TAA CCT ATT CAA GAG ATA GGT TAC GTG TCC AGA GGT TTT TTC TAG AG-3' (SEQ ID NO: 2).

Aspect 76. A method of generating a tumor killing population of cells comprising admixing NR2F6 inhibited T cells with monocytes, allowing said T cells to induce monocyte activation and said monocytes to feedback activatory signals to said T cells.

Aspect 77. The method of Aspect 76, wherein said monocytes are type 1 monocytes.

Aspect 78. The method of Aspect 76, wherein said monocyte activatory signal produced by said T cells is IL-17.

Aspect 79. The method of Aspect 76, wherein said T cell activatory signal produced by said monocyte is IL-12.

DESCRIPTION OF THE INVENTION

The invention provides inhibition of NR2F6 as a means of stimulating antitumor activity through production of IL-17. In one embodiment, IL-17 produced in response to down-regulation of NR2F6 causes an increase in macrophage cytotoxic activity to tumor cells, upregulation of NK tumor cytotoxicity, and reduction of tumor volumes as a result of direct T cell cytotoxicity.

The term "oligonucleotide" is intended to include unmodified DNA or RNA or modified DNA or RNA. For example, the nucleic acid molecules or polynucleotides of the disclosure can be composed of single- and double stranded DNA, DNA that is a mixture of single- and double-stranded regions, single- and double-stranded RNA, and RNA that is a mixture of single- and double-stranded regions, hybrid molecules comprising DNA and RNA that may be single-stranded or, more typically double-stranded or a mixture of single- and double-stranded regions. In addition, the nucleic acid molecules can be composed of triple-stranded regions comprising RNA or DNA or both RNA and DNA. The nucleic acid molecules of the disclosure may also contain one or more modified bases or DNA or RNA backbones modified for stability or for other reasons. "Modified" bases include, for example, tritiated bases and unusual bases such as inosine. A variety of modifications can be made to DNA and RNA; thus "nucleic acid molecule" embraces chemically, enzymatically, or metabolically modified forms. The term "polynucleotide" shall have a corresponding meaning.

The term "animal" as used herein includes all members of the animal kingdom, preferably mammal. The term "mammal" as used herein is meant to encompass, without limitation, humans, domestic animals such as dogs, cats, horses, cattle, swine, sheep, goats, and the like, as well as wild animals. In an embodiment, the mammal is human.

The term "interfering RNA" or "RNAi" or "interfering RNA sequence" refers to double-stranded RNA (i.e., duplex RNA) that targets (i.e., silences, reduces, or inhibits) expression of a target gene (i.e., by mediating the degradation of mRNAs which are complementary to the sequence of the interfering RNA) when the interfering RNA is in the same cell as the target gene. Interfering RNA thus refers to the double stranded RNA formed by two complementary strands or by a single, self-complementary strand. Interfering RNA typically has substantial or complete identity to the target gene. The sequence of the interfering RNA can correspond to the full length target gene, or a subsequence thereof. Interfering RNA includes small-interfering RNA" or "siRNA," i.e., interfering RNA of about 15-60, 15-50, 15-50, or 15-40 (duplex) nucleotides in length, more typically about, 15-30, 15-25 or 19-25 (duplex) nucleotides in length, and is preferably about 20-24 or about 21-22 or 21-23 (duplex) nucleotides in length (e.g., each complementary sequence of the double stranded siRNA is 15-60, 15-50, 15-50, 15-40, 15-30, 15-25 or 19-25 nucleotides in length, preferably about 20-24 or about 21-22 or 21-23 nucleotides in length, and the double stranded siRNA is about 15-60, 15-50, 15-50, 15-40, 15-30, 15-25 or 19-25 preferably about 20-24 or about 21-22 or 21-23 base pairs in length). siRNA duplexes may comprise 3' overhangs of about 1 to about 4 nucleotides, preferably of about 2 to about 3 nucleotides and 5' phosphate termini. The siRNA can be chemically synthesized or maybe encoded by a plasmid (e.g., transcribed as sequences that automatically fold into duplexes with hairpin loops). siRNA can also be generated by cleavage of longer dsRNA (e.g., dsRNA greater than about 25 nucleotides in length) with the *E. coli* RNase III or Dicer. These enzymes process the dsRNA into biologically active siRNA. (see, e.g., Yang et al., *PNAS USA* 99: 9942-7 (2002); Calegari et al., *PNAS USA* 99: 14236 (2002); Byrom et al., *Ambion Tech Notes* 10(1): 4-6 (2003); Kawasaki et al., *Nucleic Acids Res.* 31: 981-7 (2003); Knight and Bass, *Science* 293: 2269-71 (2001); and Robertson et al., *J. Biol. Chem.* 243: 82 (1968)). Preferably, dsRNA are at least 50 nucleotides to about 100, 200, 300, 400 or 500 nucleotides in length. A dsRNA may be as long as 1000, 1500, 2000, 5000 nucleotides in length, or longer. The dsRNA can encode for an entire gene transcript or a partial gene transcript.

The term "siRNA" refers to a short inhibitory RNA that can be used to silence gene expression of a specific gene. The siRNA can be a short RNA hairpin (e.g. shRNA) that activates a cellular degradation pathway directed at mRNAs corresponding to the siRNA. Methods of designing specific siRNA molecules or shRNA molecules and administering them are known to a person skilled in the art. It is known in the art that efficient silencing is obtained with siRNA duplex complexes paired to have a two nucleotide 3' overhang. Adding two thymidine nucleotides is thought to add nuclease resistance. A person skilled in the art will recognize that other nucleotides can also be added.

The term "antisense nucleic acid" as used herein means a nucleotide sequence that is complementary to its target e.g. a NR2F6 transcription product. The nucleic acid can comprise DNA, RNA or a chemical analog, that binds to the messenger RNA produced by the target gene. Binding of the antisense nucleic acid prevents translation and thereby inhibits or reduces target protein expression. Antisense nucleic acid molecules may be chemically synthesized using naturally occurring nucleotides or variously modified nucleotides designed to increase the biological stability of the molecules or to increase the physical stability of the duplex formed with mRNA or the native gene e.g. phosphorothioate derivatives and acridine substituted nucleotides. The antisense sequences may be produced biologically using an expression vector introduced into cells in the form of a recombinant plasmid, phagemid or attenuated virus in which antisense sequences are produced under the control of a high efficiency regulatory region, the activity of which may be determined by the cell type into which the vector is introduced.

As used in this context, to "treat" means to ameliorate at least one symptom of the disorder. In some embodiments, a treatment can result in a reduction in tumor size or number, or a reduction in tumor growth or growth rate.

Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast and origin.

As used herein, the terms "cancer", "hyperproliferative" and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The terms "cancer" or "neoplasms" include malignancies of the various organ systems, e.g., affecting the nervous system, lung, breast, thyroid, lymphoid, gastrointestinal, and genito-urinary tract, as well as adenocarcinomas, which include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. In some embodiments, the disease is renal carcinoma or melanoma. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation.

The inhibition of NR2F6 according to the present invention can be used for immunotherapies in a cancer patient, in particular for the activation of the immune system or the innate immune system, specifically mediated by NK cells, through upregulation of IL-17. In particular, the method according to the present invention may be employed in the patient for the treatment of cancer, the activation of NK cells according to the present invention may be combined with conventional therapies. Many tumor therapies, such as radiation therapy, chemotherapy or the surgical removal of tumors have been established for years and are constantly being refined and improved. New therapies comprise immunotherapies and therapies that are directed against specific markers of tumor cells, in particular with the use of monoclonal antibodies. Particularly the effect of the latter is largely dependent on the activity of NK cells that recognize the tumor cell-bound antibodies via general antibody determinants and consequently kill the tumor cell. The activation of the innate immune system via the effect of NK cells thus provides a further strategy that is able to complement and complete the already existing approaches in order to promote immune reactions on a broad scale, in particular for combating cancer cells. In particular, therapies that have a direct cytotoxic effect on tumor cells, such as chemotherapy or radiation therapy, are able to induce the expression of molecules of the MHC class and other immune-activating receptors, for example those of NKG2D ligands. These cellular changes are recognized by the cells of the innate immune system, in particular by NK cells, and lead to the activation thereof, by means of which it is possible to achieve a much stronger therapeutic effect owing to the synergy with the NK cell activation according to the present invention.

Preferably, the function of NR2F6 is reduced or inhibited by reducing or inhibiting the expression of NR2F6 mRNA.

The terms "reduce/reduction" or "inhibit/inhibition" relate to a reduction or inhibition of the function (or expression) of NR2F6 as compared to the unmodified natural function, optionally including the complete inhibition of said function. Preferably, the function (or expression) is reduced by at least 30%, 40%, 50%, 60%, 70%, 80%, 90% or 95%.

In preferred embodiments of the present invention, the reduction or inhibition of the function of NR2F6 is transient, i. e. the function is only temporarily reduced as described in the above and can therefore recover again, e. g. by consumption or degradation of inhibitors, such as NR2F6 siRNA, or by restructuring or non-NR2F6-impaired cells in vivo. The transient reduction of NR2F6 in immune cells can also be performed in a repetitive manner, e. g. until a therapeutic success has been achieved.

Preferably, the expression of NR2F6 is reduced or inhibited by the use of NR2F6 antisense RNA or siRNA. For this purpose, short DNA and/or RNA sequences that are complementary to one of the regions of the target (NR2F6) mRNA sequence are employed, so that hybridization and inactivation of the corresponding sequences will occur. These sequences preferably have a length of at least 15, 18, 20, 22, 25, 28, 30, 35, 40, 50, 60, 70, 80, 90, 100, 120, 140, 160, 180 or up to 200 bases until the length of the complete target sequence is reached, preferably up to 2500, 2000, 1500, 1000, 500 or 300 bases. Preferably, the sequences of SEQ ID Nos. 1, 2, 3, 4, 5, 6, 7 and/or 8 are used.

The function of NR2F6 can also be reduced or inhibited by a plurality of other known components, e. g. by the use of NR2F6 antagonists, inhibitors, in particular aptamers or intramers. According to the present invention, any antagonists or inhibitors that are capable of suppressing the effect or function of NR2F6 can be used to enhance the immunoreactivity of NK cells. For the inhibition of NR2F6, substances may be used that either specifically inhibit the zinc finger activity or inhibit the intracellular association of NR2F6 with its interaction partners or inhibit the expression of NR2F6. Preferably, antagonists or inhibitors can be used for the preparation of a pharmaceutical agent for increasing the immunoreactivity of the NK cells according to the present invention. In particular augmentation of NK cells by virtue of IL-17 induction, which results in direct and indirect stimulation of NK cell activation. Treatments of diseases with a suppressed or inefficient immune system, in particular cancer or chronic infections, are facilitated.

According to the present invention it was found that the inhibition of NR2F6 together with further NK cell-stimulatory substances (NK cell activators) induces a synergistic effect that exceeds the effect that is to be expected based on the additive effects of the inhibition of NR2F6 and the activation of NK cells. Therefore, the administration of the NR2F6 inhibitor or the inhibition of NR2F6 is preferably carried out together with a further NK cell-stimulatory substance (NK cell activator). In the following, the terms "NK cell-stimulatory substance", "NK cell-activating substance" and "NK cell activator" are used interchangeably. Such an NK cell-stimulatory substance is a substance that differs from the NR2F6 inhibitor according to the present invention. An NK cell-stimulatory substance according to the present invention is a substance which induces the activation or stimulation of NK cells in one or more suitable in vitro assays. Preferably, the NK cell-stimulatory substance induces the production of IFN-gamma and/or TNF-alpha and/or the surface expression of CD107a by the NK cells in a manner independent of the inhibition of NR2F6. Such production of IFN-gamma and/or TNF-alpha and/or surface expression of CD107a can be measured using methods known in the art (Fauriat Blood. 2010 Mar. 18; 115 (11): 2167-76; Dons'koi et al., J. Immunol. Methods 2011 Sep. 30; 372 (1-2): 187-95) or as is described in the Examples of the present application. Likewise, the effect of the NK cell-stimulatory agents may be tested by directly determining the cytotoxicity or "killing activity" of the NK cells (as described in Example 4; other suitable methods are well known in the art (Beano et al., J. Transl. Med. 2008 May 16; 6: 25; Claus et al., J. Immunol. Methods 2009 Feb. 28, 341 (1-2): 154-64; Fujisaki et al., Cancer Res. 2009 May 1, 69 (9): 4010-7; Cho et al., Clin. Cancer Res. 2010 Aug. 1, 16 (15): 3901-9), i. e. the cytotoxicity of NK cells and PBMCs, respectively, against specific target cells (SKBR3 tumor cells in Example 4) is determined, e. g. by measuring the release of the enzyme LDH from the tumor cell cytosol as a measure for the degree of cell lysis. In a corresponding in vitro measurement, the NK cells are preferably activated or stimulated in order to be able to measure the effect of the inhibition of NR2F6, e. g. by contacting with tumor cells (e. g. K562) and/or by using a NK cell-stimulatory substance (e. g. one or more cytokines, such as IL-2 and/or IL-12) and/or an antibody (e. g. trastuzumab (Herceptin®)).

In a specific embodiment, the present invention relates to the co-administration of the NR2F6 inhibitor and an NK cell activator, in particular selected from an immune cell-stimulatory cytokine, e. g. a cytokine selected from the common gamma-chain cytokines, in particular IL-2, IL-15 and IL-21 [13, 14]; cytokines that stimulate both the cells of the adaptive and of the innate immune system, in particular IL-12, IL-23 and IL-27; effector cell cytokines, such as IL-1, IL-17 and IL-17; an interferon, in particular interferon-alpha; or an interferon stimulator; an antibody, in particular an antibody which recognizes tumor cell surface molecules and/or an antibody whose constant region is capable of binding to the corresponding Fc receptor on NK cells; or a TLR or PAMP receptor ligand, in particular agonists, preferably of TLR-1[15-17], TLR-2 [18-21], TLR-3 [22, 23], TLR-7 [24], TLR-8 [25, 26], and TLR-9 [27, 28], as well as combinations of the above-mentioned NK cell activators. The terms "simultaneous" or "together with" or "in combination with" or "combined with" as used in the context of the administration of the substances according to the present invention refer to the administration of at least one NR2F6 inhibitor and at least one NK cell activator in a patient, which may be conducted in the form of one (containing at least one NR2F6 inhibitor and at least one NK cell activator) or more different pharmaceutical compositions (one of which contains at least one NR2F6 inhibitor and the other at least one NK cell activator and optionally other pharmaceutical compositions). If the administration is carried out using a plurality of different pharmaceutical compositions, the co-administration may be conducted simultaneously or sequentially. Particularly preferably, the administration of the NR2F6 inhibitor is carried out in combination with at least one NK cell activator, in particular IL-2, IL-15, IL-12, IL-23, interferon, an interferon stimulator, imiquimod and other TLR7/8 agonists, e. g. resiquimod, ssPolyU nucleotides, loxoribine, gardiquimod, CL075, CL097, CL264, 3M002, poly (I:C) oligonucleotides, CpG oligonucleotides, CD205 ligands or CD206 ligands, as well as combinations thereof. Preferred combinations of NK cell activators that may be combined with the administration of the NR2F6 inhibitor comprise, e. g., a cytokine of the common gamma-chain cytokines in combination with another of the above-mentioned NK cell activators; or a cytokine of the both the adaptive and the innate immune system in combination with another of the above-mentioned NK cell activators. Particularly preferred combinations are those involving a cytokine of the common gamma-chain cytokines and a cytokine of both the adaptive and the innate immune system, in particular IL-2 and IL-12.

According to the present invention, stimulation of anti-cancer immunity can be obtained by inhibition of NR2F6 while concurrently administering a cytokine of the common gamma-chain cytokines which is selected from the family of cytokines that share the so-called common cytokine receptor gamma-chain (.gamma..sub.c or CD132) in their receptor complexes and consists of different members having a similar structure with four alpha-helical bundles. This family includes, e. g., interleukin (IL)-2, IL-4, IL-7, IL-9, IL-15, IL-21 and thymic stromal lymphopoietin (TSLP). An immune cell-stimulatory cytokine, a cytokine of both the adaptive and the innate immune system, an effector cell cytokine or an interferon stimulator according to the present invention are preferably selected from the group comprising IL-1, IL-2, IL-3, IL-4, IL-5, IL-6, IL-7, IL-8, IL-9, IL-11, IL-12, IL-13, IL-14, IL-15, IL-16, IL-17a, IL-17f, IL-17, IL-19, IL-20, IL-21, IL-22, IL-23, IL-24, IL-25, IL-26, IL-27, IL-28, IL-29, IL-30, IL-31, IL-32, IL-33, IL-34, IL-35, IFN-alpha, IFN-beta, IFN-gamma, IFN-lambda, TNF-alpha and TNF-beta. In a particularly preferred embodiment, the present invention relates to the administration of a NR2F6 inhibitor in combination with IL-2, optionally with one or more further NK cell activators, in particular IL-12, IL-23, IFN-alpha and/or IFN-beta. In a further particularly preferred embodiment, the present invention relates to the administration of a NR2F6 inhibitor in combination with IFN-alpha, optionally with one or more further NK cell activators, in particular IL-15 and/or IL-21. In a further particularly preferred embodiment, the present invention relates to the administration of a NR2F6 inhibitor in combination with IL-12, optionally with one or more further NK cell activators, in particular IL-15 and/or IL-7. Preferably, the NK cell-stimulatory substances used induce in NK cells the production of IFN-gamma and/or TNF-alpha and/or an increased surface expression of CD107a and/or an increased cytotoxicity against the target cells. IFN-alpha, IL-12 or IL-23, for instance, induce particularly strong IFN-gamma responses in NK cells. Surprisingly, it was now found that the activation of NK cells by the inhibition of NR2F6 with NK cell-stimulatory substances that induce the production of IFN-gamma evoke particularly strong synergistic effects that go far beyond the expected effect of the individual substances.

Preferably, the NR2F6 inhibitor is coupled to a ligand of an NK cell recognition molecule, e. g. an NK cell surface molecule. Such a ligand can, for example, be a naturally occurring protein, a further biomolecule or a functional derivative thereof which is capable of binding to NK cells. In particular, such a ligand may be an antibody directed against an NK cell recognition molecule. According to the present invention, the NK cells are preferably specifically activated by the inhibition of NR2F6 in vivo, e. g. by coupling to a ligand of such an NK cell recognition molecule. The "specific" NK cell activation is to be understood as an effect on NK cells that is enhanced as compared to the non-specific, e. g. non-controlled or non-coupled, administration of a NR2F6 inhibitor, which may also have an effect in other cells. In particular, the "specific" NK cell activation is defined as an effect that is particularly directed to NK cells, as compared to the administration of a NR2F6 inhibitor alone (without the co-administration of an NK cell activator) or as compared to the administration of a NR2F6 inhibitor which is not coupled to a ligand of an NK cell recognition molecule. A nonspecific administration is carried out, e. g., by simple administration of the inhibitor without an additional administration of NK cell stimulators or NK cell-specific modifications of the inhibitor achieved by coupling to an NK cell recognition molecule. By means of the specific NK cell activation it is possible to control the NK cell-mediated immune response according to the present invention (innate immune system) with less undesired side effects which may, e. g., be caused by the adaptive immune system.

In a further aspect, the present invention relates to a pharmaceutical composition comprising a NR2F6 inhibitor and an additional NK cell activator, as described above, in particular an immune cell-stimulatory cytokine, an interferon or an interferon stimulator, an antibody or a TLR or PAMP receptor ligand. Such a composition can be used for the above-mentioned purpose of inhibiting NR2F6, either alone or in combination with further NK cell activators.

Example 1

NR2F6 Silencing Stimulates T Cell 17 Production in Response to Signal 1 and Signal 2 Activation Peripheral blood mononuclear cells (PBMC) were extracted from healthy volunteers using the Ficoll method. PBMC were resuspended in solution from Nucleofector kit and program X-01 following the Amaxa guidelines for cellular transfection. In brief, up to 1-3×10(7) cells where mixed with 1.5 mM of synthetic siRNA sequences or scrambled control sequences (Dharmacon) and were nucleofected with the Amaxa Nucleofector apparatus and immediately transferred into 37C prewarmed culture medium and cultured for a minimum of 24 hr before experimental analysis. Cells were subsequently incubated with anti-CD3 anti-CD28 beads (Xcyte) for 48 hours and IL-17 production was assessed by ELISA. As shown in FIG. 1, augmentation of T cell IL-17 induced by anti-CD3 and anti-CD28 was achieved by inhibition of NR2F6.

The invention claimed is:

1. A method of generating a population of T cells and monocytes comprising: admixing NR2F6 inhibited T cells with monocytes in vitro, allowing said T cells to secrete IL-17 and induce monocyte activation and said monocytes to feedback activatory signals comprising secretion of IL-12 to said T cells; wherein prior to said admixing, the T cells express a T cell receptor that can recognize an antigen from a predetermined tumor; and wherein said inhibition of NR2F6 is achieved by a method selected from the group consisting of: a) antisense inhibition utilizing oligonucleotides complementary to a target NR2F6 mRNA; b) induction of RNA interference to a target NR2F6 mRNA by administration of a compound selected from the group consisting of: i) single-stranded small interfering molecules (ss-siRNA); ii) short interfering RNA (siRNA); and iii) short hairpin RNA (shRNA), wherein the compound comprises a guide strand sufficiently complementary to the target NR2F6 mRNA to direct RNA interference of the NR2F6 mRNA; c) NR2F6 gene-editing; d) ribozymes complementary to a target NR2F6 mRNA; and e) decoy inhibition utilizing oligonucleotides complementary to a target NR2F6 DNA site.

2. The method of claim 1, wherein said monocytes are type 1 monocytes.

3. The method of claim 1, wherein the predetermined tumor is a melanoma or hematological tumor, and further comprising administering said population of admixed T cells and monocytes to a patient suffering from a melanoma or hematological tumor in an amount sufficient to treat said melanoma or hematological tumor.

4. The method of claim 1, wherein the sequence of said ss-siRNA molecule is sufficiently complementary to a human NR2F6 mRNA sequence to direct target-specific RNAi and wherein the 5' nucleotide is 5' phosphorylated or is capable of being 5' phosphorylated in situ or in vivo.

5. The method of claim 1, wherein said siRNA comprises a sense strand and an antisense strand, wherein the antisense strand has a sequence sufficiently complementary to a NR2F6 target mRNA sequence to direct target-specific RNAi and wherein the sense strand or antisense strand is modified by the substitution of at least one internal nucleotide with a modified nucleotide, such that in vivo stability is enhanced as compared to a corresponding unmodified siRNA or such that the target efficiency is enhanced compared to a corresponding unmodified siRNA.

6. The method of claim 5, wherein the modified nucleotide is selected from the group consisting of: (a) a sugar-modified nucleotide, (b) a nucleobase-modified nucleotide, (c) a 2'-deoxy ribonucleotide present within the sense strand (d) a 2'-fluoro modified ribonucleotide, (e) a modified nucleotide selected from the group consisting of a 2'-fluoro, 2'-amino and 2'-thio modified ribonucleotide, (f) a modified nucleotide selected from the group consisting of: 2'-fluoro modified ribonucleotide and a 2'-deoxy ribonucleotide, (g) a modified nucleotide selected from the group consisting of 2'-fluoro-cytidine, 2'-fluoro-uridine, 2'-fluoro-adenosine, 2'-fluoro-guanosine, 2'-amino-cytidine, 2'-amino-uridine, 2'-amino-adenosine, 2'-amino-guanosine, and 2'-amino-butyryl-pyrene-uridine, (h) a modified nucleotide selected from the group consisting of: 5-bromo-uridine, 5-iodo-uridine, 5-methyl-cytidine, ribo-thymidine, 2-aminopurine, 5-fluoro-cytidine, 5-fluoro-uridine, 2,6-diaminopurine, 4-thio-uridine, and 5-amino-allyl-uridine, and (i) a backbone-modified nucleotide.

7. The method of claim 1, wherein one strand of said interfering RNA compound is comprised of the nucleotide sequence: SEQ ID NO 1: 5'-GAT CCG CAT TAC GGT GTC TTC ACC TTC AAG AGA GGT GAA GAC ACC GTA ATG CTT TTT TCT AGA G-3'.

8. The method of claim 1, wherein one strand of said interfering RNA compound is comprised of the nucleotide sequence: SEQ ID NO 2: 5'-GAT CCG CCT CTG GAC ACG TAA CCT ATT CAA GAG ATA GGT TAC GTG TCC AGA GGT TTT TCT AG AG-3'.

* * * * *

SEQUENCE LISTING

<160> NUMBER OF SEQ ID NOS: 2

<210> SEQ ID NO 1
<211> LENGTH: 64
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 1
gatccgcatt acggtgtctt caccttcaag agaggtgaag acaccgtaat gcttttttct    60
agag                                                                 64

<210> SEQ ID NO 2
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gatccgcctc tggacacgta acctattcaa gagataggtt acgtgtccag aggtttttc     60 tagag                                                                65
```